(12) United States Patent
Odachi

(10) Patent No.: US 8,321,142 B2
(45) Date of Patent: Nov. 27, 2012

(54) ANALYZER, ANALYSIS METHOD AND COMPUTER PROGRAM PRODUCT

(75) Inventor: Kaoru Odachi, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 922 days.

(21) Appl. No.: 12/339,480

(22) Filed: Dec. 19, 2008

(65) Prior Publication Data

US 2009/0150083 A1  Jun. 11, 2009

Related U.S. Application Data

(63) Continuation of application No. PCT/JP2007/062049, filed on Jun. 14, 2007.

(30) Foreign Application Priority Data

Jun. 19, 2006 (JP) ................. 2006-169194

(51) Int. Cl.
*G01N 33/48* (2006.01)

(52) U.S. Cl. ........................................................ 702/19

(58) Field of Classification Search ...................... 702/19
See application file for complete search history.

(56) References Cited

FOREIGN PATENT DOCUMENTS

| | | |
|---|---|---|
| JP | 58-105065 A | 6/1983 |
| JP | 64-091061 | 4/1989 |
| JP | H02-016875 | 4/1990 |
| JP | 2000-275249 | 10/2000 |
| JP | 2003-57248 A | 2/2003 |
| JP | 2006-17600 A | 1/2006 |
| WO | WO 2004/092706 A2 | 10/2004 |

*Primary Examiner* — Jerry Lin
(74) *Attorney, Agent, or Firm* — Kilpatrick Townsend & Stockton LLP

(57) ABSTRACT

An analyzer includes a determining unit that determines whether an analysis result of a sample corresponding to a controlled specimen having a known value is normal or not based on an analysis result of the controlled specimen. The analyzer also includes a generating unit that generates analysis information in which a determination result by the determining unit is associated with each analysis result of samples; and an output unit that outputs the analysis information generated by the generating unit.

9 Claims, 14 Drawing Sheets

| SAMPLE\ITEM | | A | | A | |
|---|---|---|---|---|---|
| Q1 | | + | NORMAL | − | AB-NORMAL |
| S1 | 1 | − | ○ | + | × |
| | 2 | − | ○ | − | × |
| | 3 | − | ○ | + | × |
| | 4 | + | ○ | + | × |
| | ⋮ | ⋮ | ⋮ | ⋮ | ⋮ |
| Q2 | | + | NORMAL | − | AB-NORMAL |
| S2 | 1 | − | ○ | − | × |
| | 2 | − | ○ | − | × |
| | 3 | − | ○ | + | × |
| | ⋮ | ⋮ | ⋮ | ⋮ | ⋮ |

| SAMPLE \ ITEM | | A | | A | |
|---|---|---|---|---|---|
| Q1 | | + | NORMAL | − | AB-NORMAL |
| S1 { S11 | 1 | − | ○ | + | × |
| | 2 | − | ○ | − | × |
| | 3 | + | ○ | + | × |
| | 4 | − | ○ | − | × |
| | ⋮ | ⋮ | ⋮ | ⋮ | ⋮ |
| S12 | 101 | − | × | − | × |
| | 102 | − | × | − | × |
| | ⋮ | ⋮ | × | ⋮ | × |

| SAMPLE \ ITEM | L1 A | | L2 A | | L3 A | | L4 A | |
|---|---|---|---|---|---|---|---|---|
| Q1 | + | NORMAL | + | NORMAL | − | AB-NORMAL | − | AB-NORMAL |
| Q2 | + | NORMAL | − | AB-NORMAL | + | NORMAL | − | AB-NORMAL |
| S1 | 1 | − | ○ | − | × | − | × | + | × |
| | 2 | − | ○ | − | × | − | × | − | × |
| | 3 | − | ○ | + | × | − | × | + | × |
| | ⋮ | ⋮ | ⋮ | ⋮ | ⋮ | ⋮ | ⋮ | ⋮ | ⋮ |

Y25  Y26  Y27  Y28

ANALYZER, ANALYSIS METHOD AND COMPUTER PROGRAM PRODUCT

CROSS-REFERENCE TO RELATED APPLICATIONS

This application is a continuation of PCT international application Ser. No. PCT/JP2007/062049 filed on Jun. 14, 2007 which designates the United States, incorporated herein by reference, and which claims the benefit of priority from Japanese Patent Application No. 2006-169194, filed on Jun. 19, 2006, incorporated herein by reference.

BACKGROUND OF THE INVENTION

1. Field of the Invention

The present invention relates to an analyzer and an analysis method for analyzing a sample to be analyzed and a controlled specimen having a known value.

2. Description of the Related Art

An automatic analyzer is capable of simultaneously performing analysis processes for various samples and of rapidly analyzing various components with high accuracy, so that the analyzer is used in an examination in various fields such as an immunological examination, a biochemical examination, and a blood transfusion examination (for example, refer to Japanese Patent Application Laid-open No. H02-016875). The sample to be analyzed in such an automatic analyzer is a biological fluid specimen such as blood and urine of a patient, and since an analysis result thereof becomes a base of diagnosis of a disease and determination of therapeutic strategy, so that it is required to rapidly obtain the highly reliable analysis result. There is a method of measuring a controlled specimen indicating a known result with the sample, as a method of controlling an operation of the analyzer and reliability of the analysis result. This is a method of measuring the controlled specimen before and after measurement or between measurements of the sample of the patient, determining that the analyzer normally operates when the analysis result of the controlled specimen is within the known result, and certifying the analysis result of the patient sample. When the analysis result of the controlled specimen is not the known result, abnormality might occur in the analyzer, and it is not possible to certify the analysis result of the patient specimen.

SUMMARY OF THE INVENTION

An analyzer according to an aspect of the present invention includes a determining unit that determines whether an analysis result of a sample corresponding to a controlled specimen having a known value is normal or not based on an analysis result of the controlled specimen; a generating unit that generates analysis information in which a determination result by the determining unit is associated with each analysis result of samples; and an output unit that outputs the analysis information generated by the generating unit.

An analysis method according to another aspect of the present invention is for analyzing a sample and a controlled specimen having a known value. The analysis method includes determining whether an analysis result of the sample corresponding to the controlled specimen is normal or not based on an analysis result of the controlled specimen; generating analysis information in which a determination result by the determining is associated with each analysis result of samples, the each analysis result being obtained at the determining; and outputting the generated analysis information.

A computer program product according to still another aspect of the present invention causes a computer to perform the method according to the present invention.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
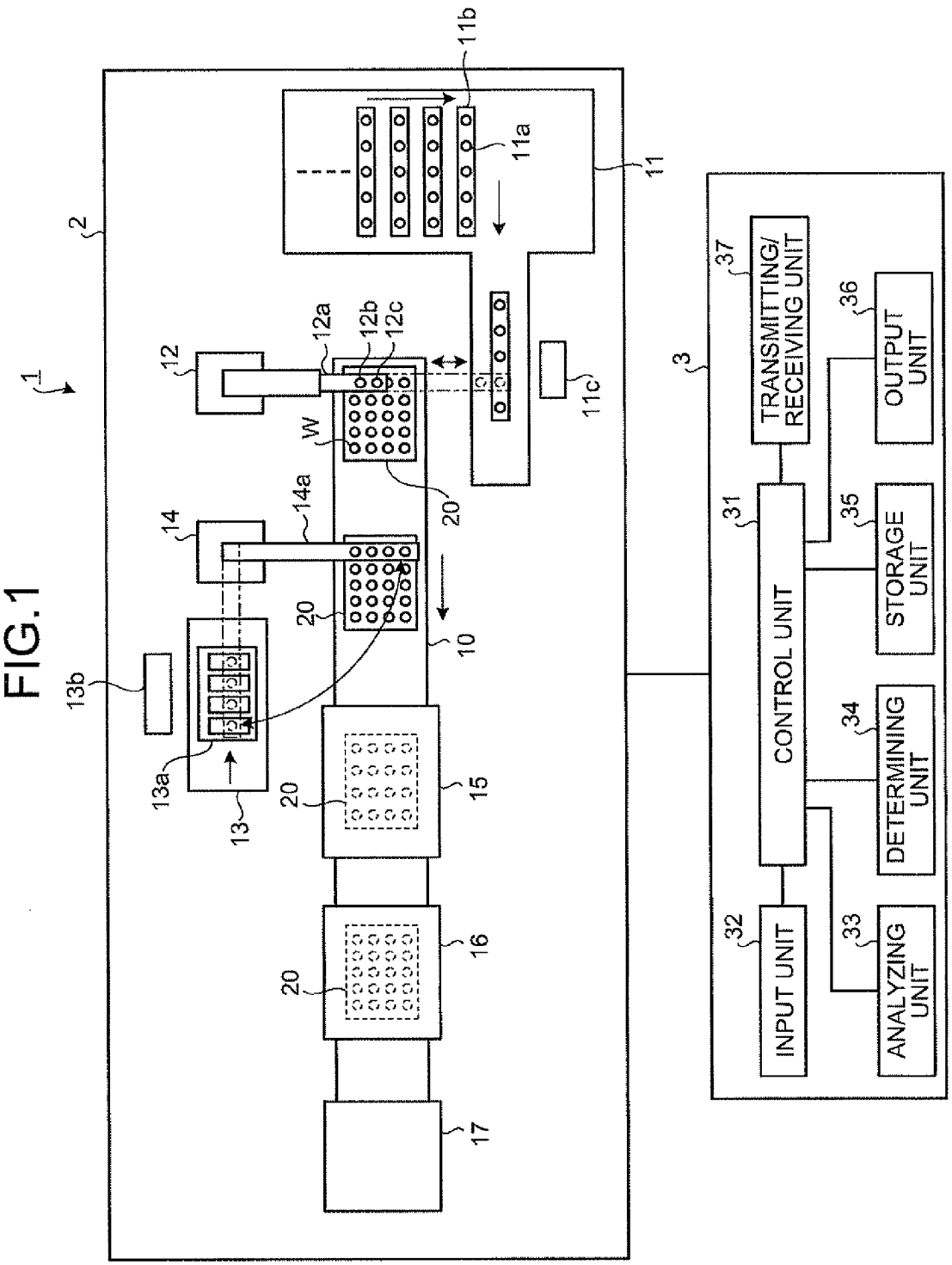
FIG. 1 is a schematic view for showing a configuration of an analyzer according to a first embodiment.

Hereinafter, an analyzer according to embodiments of the present invention is described with reference to drawings, taking an analyzer for performing an immunological examination such as an antigen-antibody reaction of test blood using immunological agglutination behavior as an example, out of fields of biochemical examination and blood transfusion examination. Meanwhile, the present invention is not limited to the embodiments. In addition, same reference numerals are assigned to same portions in the drawings.

First, a first embodiment is described. FIG. 1 is a schematic view for showing a configuration of the analyzer according to the first embodiment. As shown in FIG. 1, an analyzer 1 according to the first embodiment is provided with a measuring mechanism 2 for dispensing a sample and a reagent to be analyzed in a predetermined well W on a micro plate 20 and optically measuring a reaction occurred in the well W, and a control mechanism 3 for controlling an entire analyzer 1 including the measuring mechanism 2 and analyzing a measurement result in the measuring mechanism 2. In the analyzer 1, the two mechanisms work together to automatically perform an immunological analysis of a plurality of samples. Meanwhile, the micro plate 20 is a plate formed of a transparent material such as acrylic and has numerous holes opening on a surface thereof, which are referred to wells W. The wells W are holes in which a slant surface is formed, for accommodating the sample, and are arranged in a matrix pattern on the surface of the micro plate 20.

The measuring mechanism 2 is largely provided with a plate carrier lane 10, a sample transferring unit 11, a sample dispensing mechanism 12, a reagent transferring unit 13, a reagent dispensing mechanism 14, a reaction promoting unit 15, a light measuring unit 16, and a plate retrieving unit 17. The control mechanism 3 is provided with a control unit 31, an input unit 32, an analyzing unit 33, a determining unit 34, a storage unit 35, an output unit 36, and a transmitting/receiving unit 37. Each unit of the measuring mechanism 2 and the control mechanism 3 is electrically connected to the control unit 31.

The plate carrier lane 10 carries the micro plate 20 to a predetermined position for dispensing the sample and the reagent to each well W on the micro plate 20, and promoting the reaction and measuring light of liquid in the well W. The plate carrier lane 10 carries the micro plate 20, for example, leftward as indicated by an arrow in FIG. 1, by drive of a driving mechanism not shown under control of the control unit 31.

The sample transferring unit 11 is provided with a plurality of sample racks 11b holding a plurality of sample vessels 11a accommodating the sample and sequentially transferred in a direction indicated by an arrow in the drawing. The sample accommodated in the sample vessel 11a is obtained by separating blood taken from a sample provider into serum, which is supernatant liquid, and blood cell (red blood cell) particles, which become sediment, by adding an anticaking agent to the blood and treat the same in an ultracentrifuge. The sample in the sample vessel 11a transferred to the predetermined position on the sample transferring unit 11 is dispensed to the predetermined well W on the micro plate 20 arranged on the plate carrier lane 10 and carried by the sample dispensing mechanism 12.

A recording medium in which sample information regarding the sample accommodated in the sample vessel 11a is recorded is attached to a side of the sample vessel 11a. The recording medium indicates various pieces of coded information and is optically read. The sample information includes, for example, name, gender, age, and item to be analyzed of a patient who provided the sample.

A sample reader 11c for optically reading the recording medium is provided on a corresponding portion of the sample transferring unit 11. The sample reader 11c emits infrared light or visible light to the recording medium, and processes reflected light from the recording medium, thereby reading the information of the recording medium. Also, the sample reader 11c may obtain the information of the recording medium by performing an image process to the recording medium and reading image information obtained by the image process. The sample reader 11c reads the information of the recording medium attached to the sample vessel 11a when passing in front of the sample reader 11c.

The sample dispensing mechanism 12 is provided with an arm 12a having probes 12b and 12c for sucking and discharging the sample attached to its distal end, and a sucking/discharging mechanism using a sucking and discharging syringe or a piezoelectric device not shown. The sample dispensing mechanism 12 sucks the sample from the sample vessel 11a transferred to the predetermined position on the above-described sample transferring unit 11 by the probes 12b and 12c, moves the arm 12a upward and downward in the drawing, and discharges the sample to each well W to dispense. Meanwhile, the probe 12b sucks and discharges the serum in the sample vessel 11a, and the probe 12c sucks and discharges the red blood cell particles in the sample vessel 11a.

The reagent transferring unit 13 transfers a reagent set 13a in which the reagents to be dispensed to each well W on the micro plate 20 are accommodated to a reagent sucking position by the reagent dispensing mechanism 14. In the reagent set 13a, predetermined amounts of required reagents are accommodated depending on various items to be analyzed, and each reagent included in one reagent set 13a may be dispensed in a predetermined times or may be dispensed at once. The reagent transferring unit 13 retrieves the reagent set 13a of which dispense process in the predetermined times is finished, and transfers the reagent set 13a to be dispensed next to the reagent sucking position.

A recording medium in which reagent information regarding each reagent accommodated in the reagent set 13a is recorded is attached to a side of the reagent set 13a. The recording medium indicates various pieces of coded information and is optically read. A reagent reader 13b for optically reading the recording medium is provided on a corresponding portion of the reagent transferring unit 13. The reagent reader 13b emits the infrared light or the visible light to the recording medium, and processes reflected light from the recording medium, thereby reading the information of the recording medium. Also, the reagent reader 13b may obtain the information of the recording medium by performing the image process to the recording medium and reading image information obtained by the image process.

The reagent dispensing mechanism 14 is provided with an arm 14a having a probe that sucks and discharges the reagent attached to its distal end. The arm 14a freely vertically moves up and down and rotates about a vertical line passing through a proximal portion thereof. The reagent dispensing mechanism 14 is provided with a sucking/discharging mechanism using a sucking and discharging syringe or piezoelectric device not shown. The reagent dispensing mechanism 14 sucks the reagent in the reagent set 13a transferred to the predetermined position on the reagent transferring unit 13 by corresponding each probe, swirls the arm 14a in a clockwise direction in the drawing, and discharges each reagent corresponding to each well W on the micro plate 20 transferred to the predetermined position on the plate carrier lane 10 to perform dispensing.

The reaction promoting unit 15 promotes the reaction of the sample and the reagent dispensed to the micro plate 20 to perform the antigen-antibody reaction, thereby forming an aggregation pattern on a bottom surface of each well W on the micro plate 20. The reaction promoting unit 15, for example, shakes the micro plate 20 to stir the specimen and the reagent in the well W. Also, the reaction promoting unit 15 leaves the micro plate 20 at rest for a predetermined time period corresponding to the contents of the analysis method to promote spontaneous sedimentation of the red blood cell particles. Also, the reaction promoting unit 15 manipulates the particles in the well W by applying a predetermined magnetic field, for example.

The light measuring unit 16 measures light to detect the aggregation pattern formed by the reaction promoting unit 15. The light measuring unit 16 is composed of, for example, a CCD camera, and images each well W on the micro plate 20 from above to output the image information obtained by imaging the aggregation pattern formed in each well W. The light measuring unit 16 may be provided with a light emitter that emits predetermined light to each well W on the micro plate 20, and a light receiver that receives light generated in the sample in each well W, and output brightness of the light generated in the sample as a light measurement result.

The plate retrieving unit 17 retrieves the micro plate 20 of which light measuring process by the light measuring unit 16 is finished. The retrieved micro plate 20 is cleaned by a cleaner not shown such that mixed liquid in each well W is sucked and discharged and cleaning liquid is injected and sucked. The cleaned micro plate 20 is reused. Meanwhile, depending on contents of examination, the micro plate 20 might be discarded after finishing single measurement.

Next, the control mechanism 3 is described. The control unit 31 is composed of a CPU or the like and controls process and operation of each unit of the analyzer 1. The control unit 31 performs predetermined input and output control for information input and output to and from each component, and performs predetermined information processing to the information. The input unit 32 is formed of a keyboard, a mouse, a microphone, or the like, and obtains pieces of information required to analyze the sample, instruction information of an analysis operation, and the like, from outside.

The analyzing unit 33 analyzes the antigen-antibody reaction based on the light measurement result measured by the light measuring unit 16. Meanwhile, when the light measuring unit 16 outputs the image information, the analyzing unit 33 processes the image information output by the light measuring unit 16 to obtain a light measurement value depending on the brightness of the sample.

The determining unit 34 determines whether analysis results of the samples corresponding to a controlled specimen are normal or not, based on an analysis result of the controlled specimen measured before and after the measurement or between the measurements of the patient sample, of which analysis result is a known value, and generates analysis information in which a determination result is associated with each analysis result of the samples. The determining unit 34 determines that the analysis result of the controlled specimen is normal when the analysis result of the controlled specimen is the known value, and determines that the analysis results of the samples corresponding to the controlled specimen are normal. On the other hand, the determining unit 34 determines that the analysis result of the controlled specimen is abnormal when the analysis result of the controlled specimen is not the known value, and determines that the analysis results of the samples corresponding to the controlled specimen are abnormal. Further, the determining unit 34 determines that the analysis results of the samples within a predetermined range of the samples corresponding to the controlled specimen are normal, and determines that the analysis result of the samples out of a predetermined range are abnormal when the analysis result of the controlled specimen is the known value. The determining unit 34 determines the analysis results for the samples analyzed after the controlled specimen as the samples corresponding to the controlled specimen. The predetermined range is set depending on the contents of the analysis method for the sample. For example, the predetermined range is set depending on a volume of the reagent accommodated in the reagent set 13a, and when the volume corresponding to the dispensing amount of 100 times is accommodated in each reagent of the reagent set 13a, the range corresponding to the first sample with which the reagent dispensing is started to the $100^{th}$ sample is set. Meanwhile, the predetermined range is stored in the storage unit 35 in advance, and set based on the instruction information input from the input unit 32 and the instruction information input from a transmitting/receiving unit 37.

The storage unit 35 is composed of a hard disk for magnetically storing information, and a memory for loading various programs regarding the processing from the hard disk when the analyzer 1 executes the processing and electrically storing the same, and stores pieces of information including the analysis information generated by the determining unit 34. The storage unit 35 may be provided with a supplementary storage device capable of reading the information stored in the storage medium such as a CD-ROM, a DVD-ROM, and a PC card.

The output unit 36 is composed of a display, a printer, a speaker, and the like, and outputs pieces of information including the analysis information generated by the determining unit 34. The transmitting/receiving unit 37 serves as an interface for transmitting and receiving the information according to a predetermined format through a communication network not shown.

In the analyzer 1 thus configured, the sample dispensing mechanism 12 dispenses the sample in the sample vessel 11a and the reagent dispensing mechanism 14 dispenses each reagent in the reagent set 13a, to a plurality of sequentially carried micro plates 20, and after that, the light measuring unit 16 measures brightness of the sample in a state in which the sample and the reagent are reacted, and the analyzing unit 33 analyzes the measurement result, thereby the antigen-antibody reaction analysis or the like of the sample is automatically performed.

Figure 2:
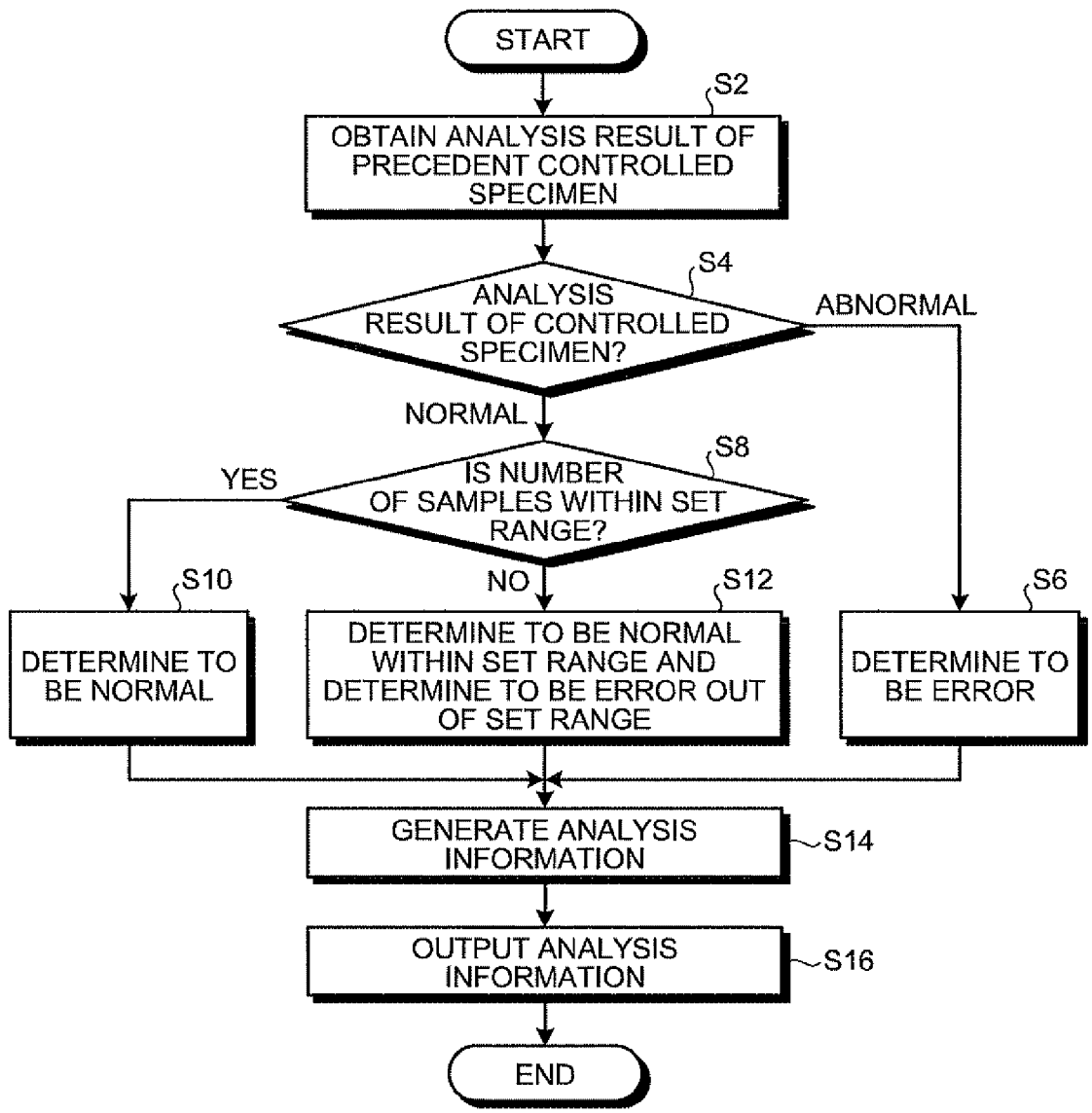
FIG. 2 is a flowchart for showing a procedure by which the analyzer shown in FIG. 1 determines an analysis result of a sample.

Next, a determination process of the analysis results of the samples by the analyzer 1 is described. FIG. 2 is a flowchart for showing a procedure by which the analyzer 1 determines the analysis result of the sample. As shown in FIG. 2, the determining unit 34 obtains the analysis result of the controlled specimen analyzed before a sample group to be determined (step S2). The determining unit 34 determines whether the analysis result of the controlled specimen is normal or not, based on whether the analysis result of the controlled specimen is the known value or not (step S4).

The determining unit 34 determines that all of the analysis results of the samples in the sample group to be determined are error (step S6) when determining that the analysis result of the controlled specimen is abnormal (step S4: abnormal). On the other hand, the determining unit 34 determines whether the number of samples in the sample group to be determined is within the predetermined set range or not (step S8) when determining that the analysis result of the controlled specimen is normal (step S4: normal).

The determining unit 34 determines that the analysis results of the samples in the sample group to be determined are normal (step S10) when determining that the number of samples in the sample group to be determined is within the predetermined set range (step S8: Yes). On the other hand, the determining unit 34 determines that the analysis results of the samples within the set range are normal, and the analysis results of the samples out of the set range are error (step S12), when determining that the number of samples in the sample group to be determined is larger than the predetermined set range and out of the predetermined set range (step S8: No). Meanwhile, the output unit 36 may perform a warning process to output a voice or a display to inform the error when the error occurs in the analysis result of the sample group to be analyzed, at steps S6 and S12.

Next, the determining unit 34 generates the analysis information in which the determination results at steps S6, S10 and S12 are associated with each analysis result of the samples (step S14) The determining unit 34 outputs the generated analysis information to the storage unit 35 and the output unit 36, and the output unit 36 outputs the analysis information (step S16). A user of the analyzer 1 may easily and rapidly recognize whether contents of the analysis result of each sample are certified or not by checking the analysis information in which each determination result is associated with the analysis results of the sample.

Figures 3, 4:
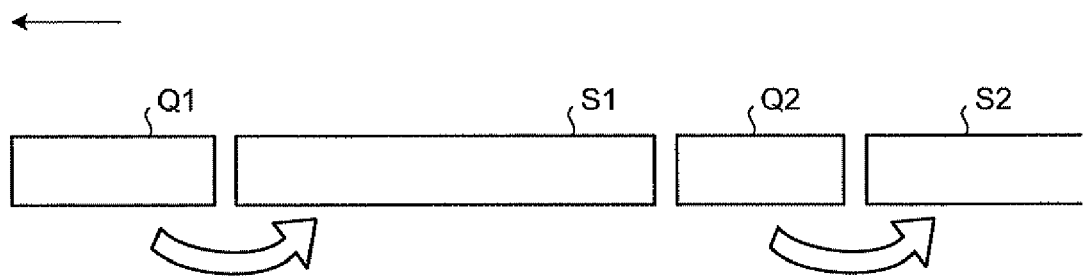
FIG. 3 is a view for illustrating a process operation in a determining unit shown in FIG. 1.
FIG. 4 is a view for illustrating the process operation in the determining unit shown in FIG. 1.

Next, the determination process of the determining unit 34 is specifically described with reference to FIGS. 3 to 6. As shown in FIG. 3, a controlled specimen group Q1, a sample group S1, a controlled specimen group Q2, and a sample group S2 are measured and analyzed in this order in a direction indicated by an arrow. The determining unit 34 reflects the analysis result of the controlled specimen group Q1 analyzed before the sample group S1 in the determination for the sample group S1, and reflects the analysis result of the controlled specimen group Q2 analyzed before the sample group S2 in the determination for the sample group S2.

As shown in a table T1 in FIG. 4, the determining unit 34 determines that the analysis process for the controlled specimen is normal when the controlled specimen group Q1 of which analysis result is positive (hereinafter, represented as "+") indicates a known value "+". In this case, the determining unit 34 determines that the analysis results of the samples in the sample group S1 are normal as indicated by an arrow Y11. On the other hand, the determining unit 34 determines that there is abnormality in the analysis process for the controlled specimen group Q1 when the controlled specimen group Q1 indicates negative (hereinafter, represented as "−") in place of the known value "+" and determines that the analysis results of the samples in the sample group S1 are abnormal as indicated by an arrow 12. In addition, also for the controlled specimen group Q2, when this indicates the known value "+", the determining unit 34 determines that the analysis results of the samples in the sample group S2 corresponding to the controlled specimen group Q2 are normal as indicated by an arrow Y13, and when this indicates "−", determines that the analysis results of the samples in the sample group S2 are abnormal as indicated by an arrow Y14.

Figures 5, 6:
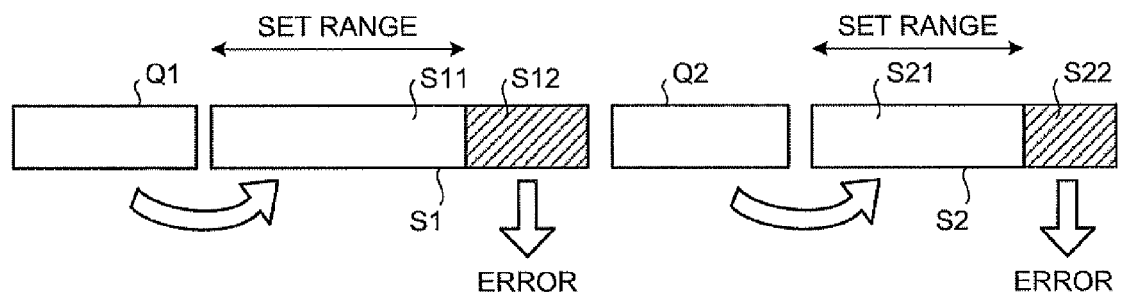
FIG. 5 is a view for illustrating the process operation in the determining unit shown in FIG. 1.
FIG. 6 is a view for illustrating the process operation in the determining unit shown in FIG. 1.

Further, as shown in FIG. 5, when the number of samples in the sample group S1 is larger than the predetermined set range, the determining unit 34 reflects the analysis result of the controlled specimen group Q1 to the sample group S11 of the sample group S1 within the set range, and determines all of the analysis results in the sample group S12 out of the set range to be error. Similarly, also in the sample group S2, the determining unit 34 reflects the analysis result of the controlled specimen group Q2 to the specimen group S21 within the set range, and determines all of the analysis results of the sample group S22 out of the set range to be error. Specifically, as shown in a table T2 in FIG. 6, when the controlled specimen group Q1 indicates "+" and it is determined to be normal, the determining unit 34 determines that the analysis results in the sample group S11 within the set range are normal as indicated by an arrow Y15 and determines that all of the analysis results of the sample group S12 out of the set range are error as indicated by an arrow Y16. Also, when the controlled specimen group Q1 indicates "−" and it is determined to be abnormal, the determining unit 34 determines that all of the analysis results in the sample group S1 are error as indicated by an arrow Y17. In the analyzer 1, the determining unit 34 generates the analysis information shown in the table T1 in FIG. 4 and the table T2 in FIG. 6, for example, as the analysis information in which the determination result are associated with the analysis result of each sample, and the output unit 36 outputs the analysis information generated by the determining unit 34.

In this manner, the analyzer 1 automatically generates the analysis information in which each determination result based on the analysis result of the controlled specimen is associated with the analysis results of the samples, and outputs the same. Therefore, in the analyzer, it is not required that the user himself manually reflect the result of the controlled specimen in the analysis results of each sample, so that it is possible to reduce the load of the user and reduce the error in the determination process occurred due to the manual process by the user. Therefore, according to the analyzer 1, the user may easily and rapidly recognize whether contents of the analysis results of each sample are certified or not by checking the correct analysis information generated by the analyzer 1, and to take appropriate response such as reexamination of the sample.

Figure 7:
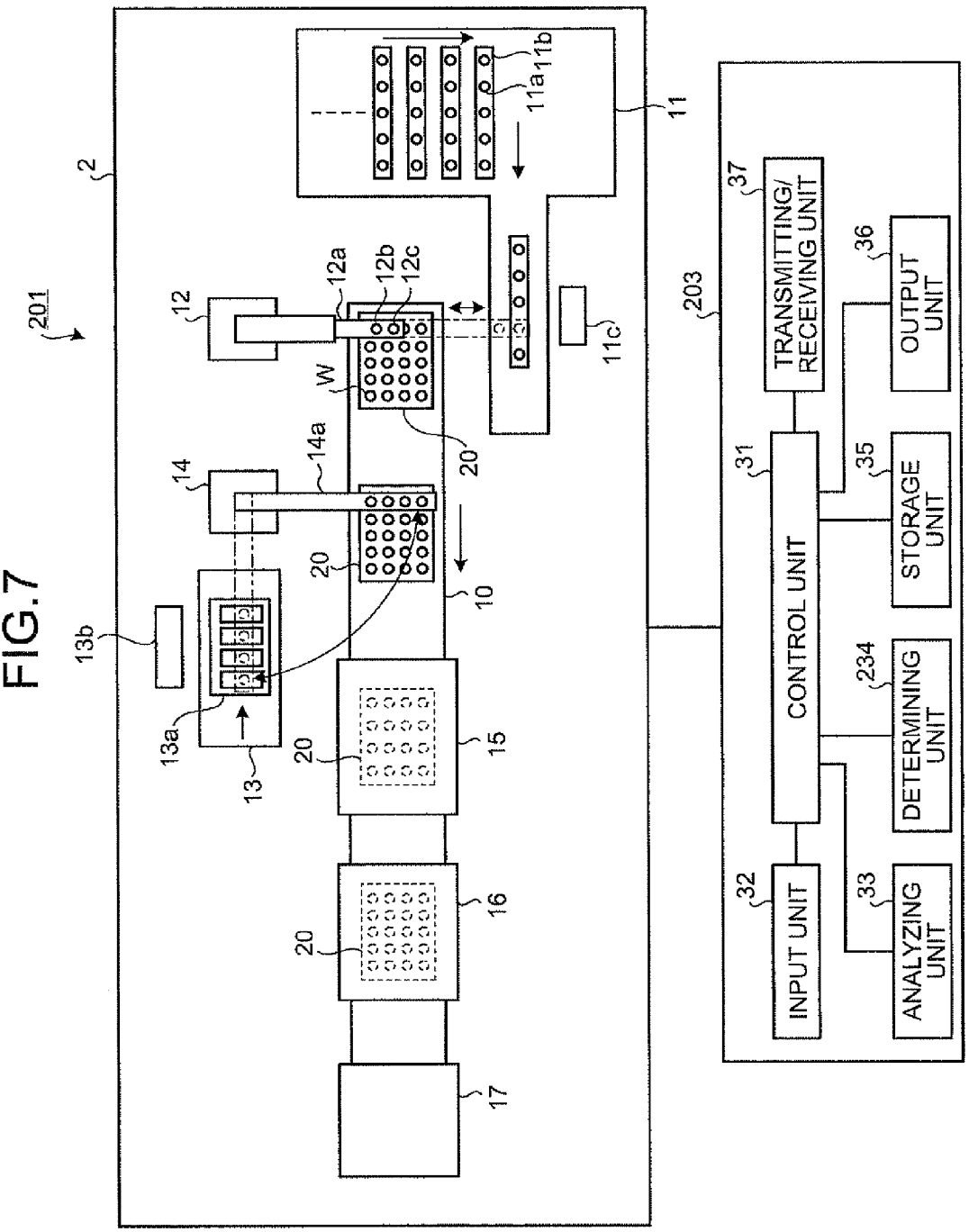
FIG. 7 is a schematic view for showing a configuration of an analyzer according to a second embodiment.

Next, a second embodiment is described. In the second embodiment, the analysis results of a plurality of controlled specimens are reflected in the analysis results of the samples to be analyzed to perform a certification process. FIG. 7 is a schematic view for showing a configuration of an analyzer according to the second embodiment.

As shown in FIG. 7, an analyzer 201 according to the second embodiment is provided with a control mechanism 203 having a determining unit 234 in place of the determining unit 34 in the analyzer 1 according to the first embodiment. The determining unit 234 determines that the analysis results of the samples are normal when both of the first and second controlled specimens indicate known values and the number of samples analyzed between the first and second controlled specimens is within the predetermined range.

Figure 8:
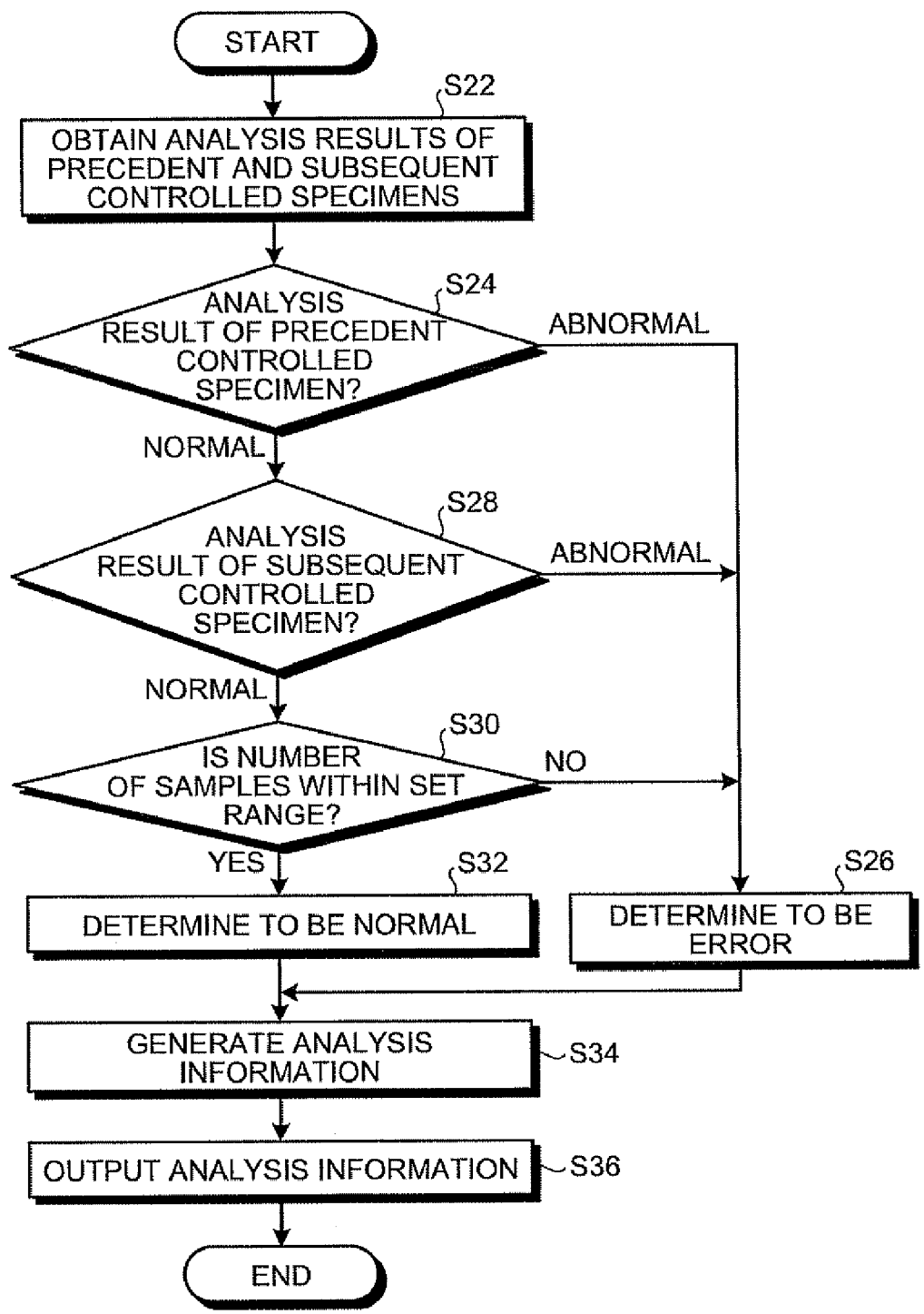
FIG. 8 is a flowchart for showing a procedure by which the analyzer shown in FIG. 7 determines an analysis result of the sample.

Next, the determination process of the analysis results of the samples by the analyzer 201 is described. FIG. 8 is a flowchart for showing a procedure by which the analyzer 201 determines the analysis result of the samples. As shown in FIG. 8, the determining unit 234 obtains the analysis results of the controlled specimens analyzed before and after the sample group to be determined (step S22). First, the determining unit 234 determines whether the analysis result of the controlled specimen analyzed before the sample group to be determined is normal or not based on whether the analysis result of the controlled specimen indicates the known value or not (step S24).

The determining unit 234 determines that all of the analysis results of the samples in the sample group to be determined are error (step S26) when determining that the analysis result of the controlled specimen analyzed before the sample group to be determined is abnormal (step S24: abnormal). On the other hand, the determining unit 234 determines whether the analysis result of the controlled specimen analyzed after the sample group to be determined is normal or not (step S28) when determining that the analysis result of the controlled specimen analyzed before the sample group to be determined is normal (step S24: normal).

The determining unit 234 determines that all of the analysis results of the samples in the sample group to be determined are error (step S26) when determining that the analysis result of the controlled specimen analyzed after the sample group to be determined is abnormal (step S28: abnormal). On the other hand, the determining unit 234 determines whether the number of samples in the sample group to be determined is within the predetermined set range or not (step S30), when determining that the analysis result of the controlled specimen analyzed after the sample group to be determined is normal (step 328: normal).

The determining unit 234 determines that all of the analysis results of the samples to be determined are error (step 326) when determining that the number of samples in the sample group to be determined is larger than the predetermined set range and out of the predetermined set range (step S30: No). Also, the determining unit 234 determines that the analysis results of the samples in the sample group to be determined are normal (step S32) when determining that the number of samples in the sample group to be determined is within the predetermined set range (step S30: Yes).

Next, as in steps S14 and S16 shown in FIG. 2, the determining unit 234 generates the analysis information in which the determination results at steps S26 and S32 are associated with each analysis result of the samples (step S34), and the output unit 36 outputs the analysis information (step S36).

Next, the determination process by the determining unit 234 is specifically described with reference to FIGS. 9 to 12. The determining unit 234 reflects the analysis results of the controlled specimen group Q1 analyzed before the sample group S1 and the controlled specimen group Q2 analyzed after the sample group S1 in the determination for the sample group S1, as indicated by arrows Y21 and Y22 in FIG. 9, and reflects the analysis results of the controlled specimen group Q2 analyzed before the sample group S2 and the controlled specimen group Q3 analyzed after the sample group S2 in the determination for the sample group S2, as indicated by arrows Y23 and Y24 in FIG. 9.

Figures 9, 10:
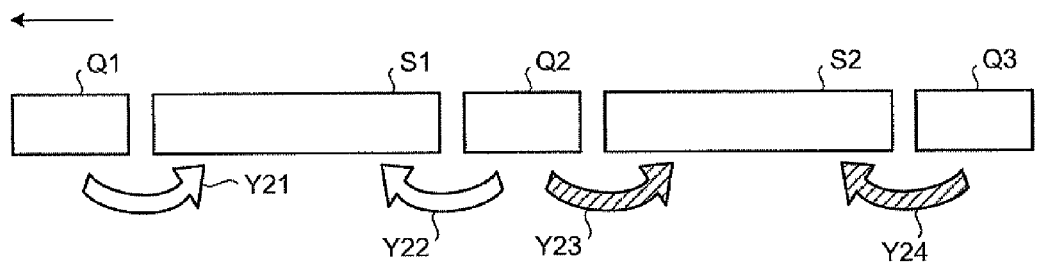
FIG. 9 is a view for illustrating a process operation in a determining unit shown in FIG. 7.
FIG. 10 is a view for illustrating the process operation in the determining unit shown in FIG. 7.

As shown in a column L1 in a table T3 in FIG. 10, the determining unit 234 determines that the analysis processes in the controlled specimen groups Q1 and Q2 are normal when both of the controlled specimen groups Q1 and Q2 indicate the known value "+". In this case, the determining unit 234 determines that the analysis results of the samples in the sample group S1 are normal as indicated by an arrow Y25. On the other hand, as shown in columns L2 to L4 in the table 3, when at least either of the controlled specimen groups Q1 and Q2 indicates "-", the determining unit 234 determines that there is abnormality in the analysis processes for the controlled specimen groups Q1 and Q2. In this case, the determining unit 234 determines that the analysis results of the samples in the sample group S1 are abnormal as indicated by arrows Y26 to Y28.

Figures 11, 12:
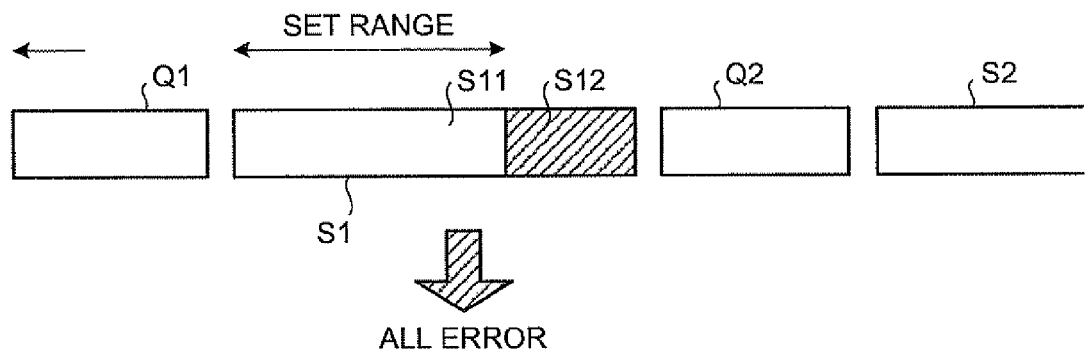
FIG. 11 is a view for illustrating the process operation in the determining unit shown in FIG. 7.
FIG. 12 is a view for illustrating the process operation in the determining unit shown in FIG. 7.

Also, as shown in FIG. 11, when the number of samples in the sample group S1 is larger than the predetermined set range, all of the samples in the sample group S1 are determined to be error. Specifically, as indicated by an arrow Y29 in a table T4 in FIG. 12, even when both of the analysis results of the controlled specimen groups Q1 and Q2 indicate "+", the determining unit 234 determines that all of the analysis results are error also for the sample group S11 within the set range in addition to the sample group S12 out of the set range, when the number of samples in the sample group S1 is larger than the set range.

In this manner, the analyzer 201 automatically generates the analysis information in which each determination result based on the analysis result of the controlled specimen is associated with the analysis results of the samples, and outputs the same, so that this has the effect similar to that of the first embodiment. Further, the analyzer 201 determines the analysis results of the sample group based on the analysis results of the controlled specimens measured before and after the sample group to be analyzed, so that it is possible to more surely certify the quality of the sample group.

Figure 13:
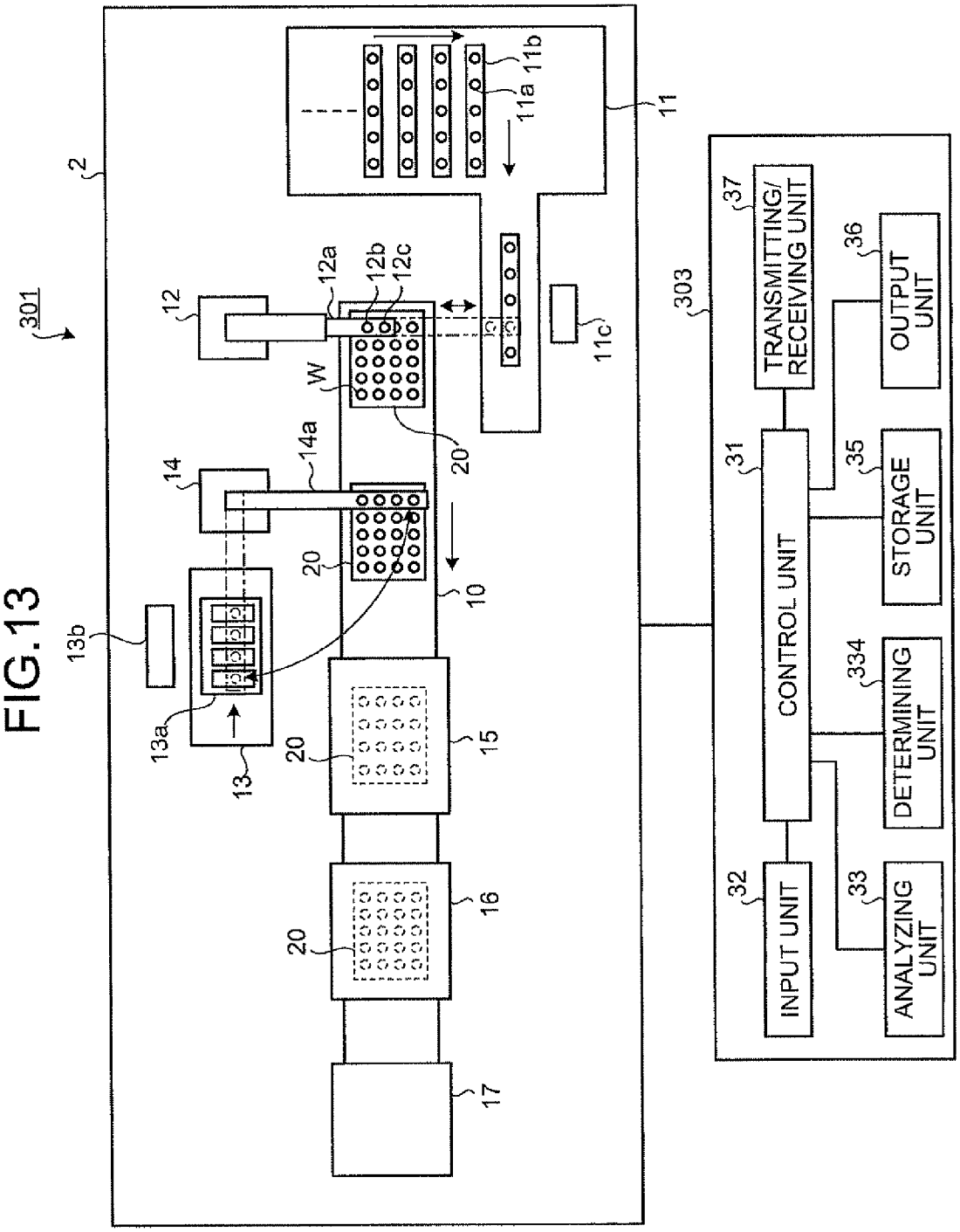
FIG. 13 is a schematic view for showing a configuration of an analyzer according to a third embodiment.

Next, a third embodiment is described. In the third embodiment, the certification process is performed by reflecting the analysis result of the controlled specimen analyzed after the sample group to the analysis result. FIG. 13 is a schematic view for showing a configuration of an analyzer according to the third embodiment.

As shown in FIG. 13, an analyzer 301 according to the third embodiment is provided with a control mechanism 303 having a determining unit 334 in place of the determining unit 34 in the analyzer 1 according to the first embodiment. The determining unit 334 determines the analysis results for the samples analyzed before the controlled specimen as the samples corresponding to the controlled specimen.

Figure 14:
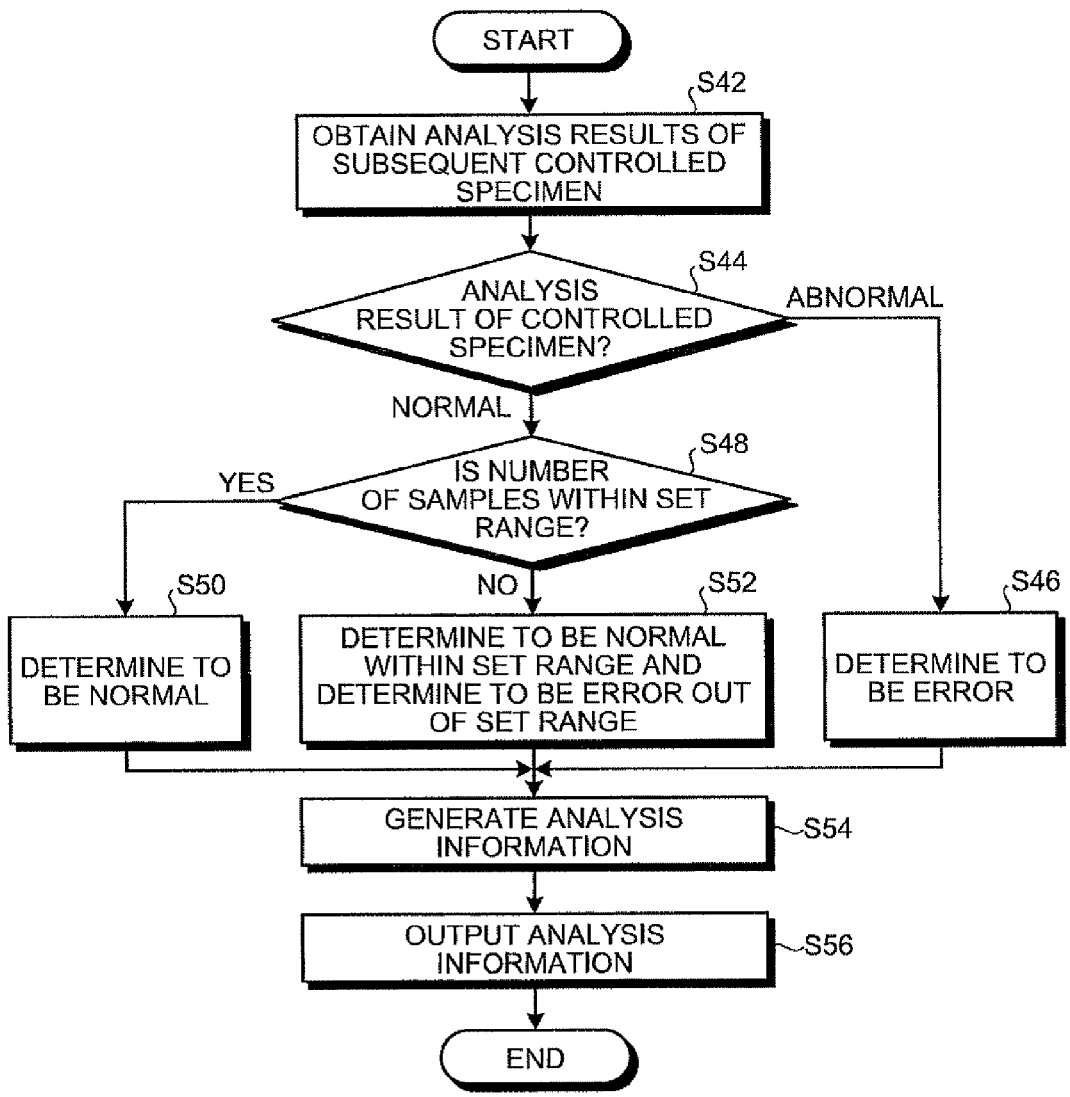
FIG. 14 is a flowchart for showing a procedure by which the analyzer shown in FIG. 13 determines an analysis result of the sample.

Next, a determination process of the analysis results of the samples by the analyzer 301 is described. FIG. 14 is a flowchart for showing a procedure by which the analyzer 301 determines the analysis results of the samples. As shown in FIG. 14, the determining unit 334 obtains the analysis result of the controlled specimen analyzed after the sample group to be determined (step S42). The determining unit 334 determines whether the analysis result of the controlled specimen is normal or not based on whether the analysis result of the controlled specimen indicates the known value or not (step S44).

The determining unit 334 determines that all of the analysis results of the samples in the sample group to be determined are error (step S46) when determining that the analysis result of the controlled specimen is abnormal (step S44: abnormal). On the other hand, the determining unit 334 determines whether the number of samples in the sample group to be determined is within the predetermined set range or not (step S48) when determining that the analysis result of the controlled specimen is normal (step S44: normal).

The determining unit 334 determines that the analysis results of the samples in the sample group to be determined are normal (step S50) when determining that the number of samples in the sample group to be determined is within the predetermined set range (step S48: Yes). On the other hand, the determining unit 334 determines that the analysis results of the samples within the set range are normal and the analysis result of the samples out of the set range are error (step S52) when determining that the number of samples in the sample group to be determined is larger than the predetermined set range and out of the predetermined set range (step S48: No).

Next, as in steps S14 and S16 shown in FIG. 2, the determining unit 334 generates the analysis information in which the determination results at steps S46, 350, and S52 are associated with each analysis result of the samples (step S54), and the output unit 36 outputs the analysis information (step S56).

Figure 15:
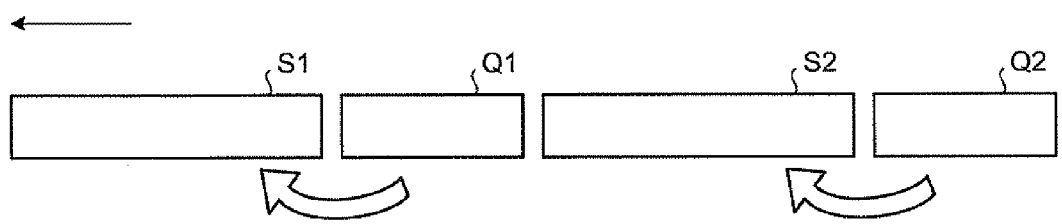
FIG. 15 is a view for illustrating a process operation in the determining unit shown in FIG. 13.

Next, the determination process of the determining unit 334 is specifically described with reference to FIGS. 15 to 18. As shown in FIG. 15, the determining unit 334 reflects the analysis result of the controlled specimen group Q1 analyzed after the sample group S1 in the determination for the specimen group 31, and reflects the analysis result of the controlled specimen group Q2 analyzed after the sample group S2 in the determination for the sample group S2.

Figure 16:
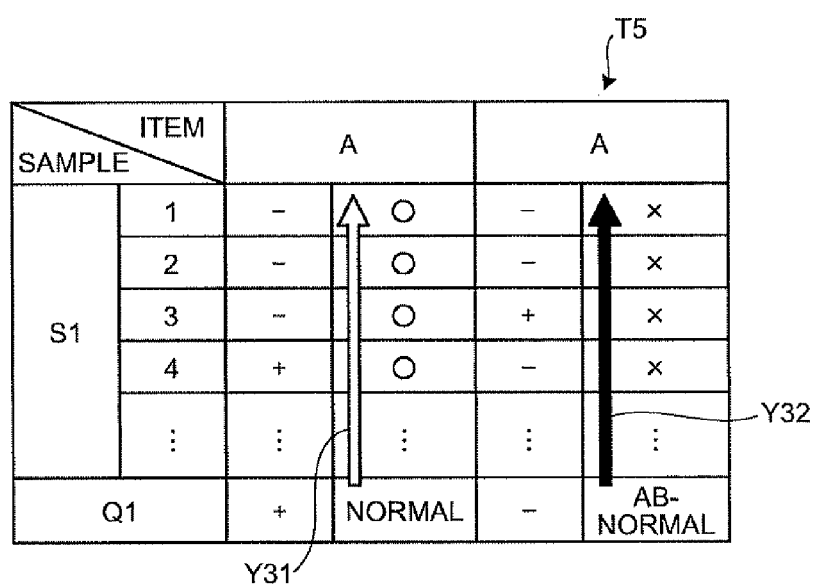
FIG. 16 is a view for illustrating the process operation in the determining unit shown in FIG. 13.

As shown in a table T5 in FIG. 16, the determining unit 334 determines that the analysis process in the controlled specimen group Q1 is normal when the controlled specimen group Q1 of which analysis result is "+" indicates "+". In this case, the determining unit 334 determines that the analysis results of the samples in the sample group S1 analyzed before the controlled specimen group Q1 are normal as indicated by an arrow Y31. On the other hand, the determining unit 334 determines that the analysis results of the samples in the sample group S1 are abnormal as indicated by an arrow Y32, when the controlled specimen group Q1 indicates "−".

Figures 17, 18:
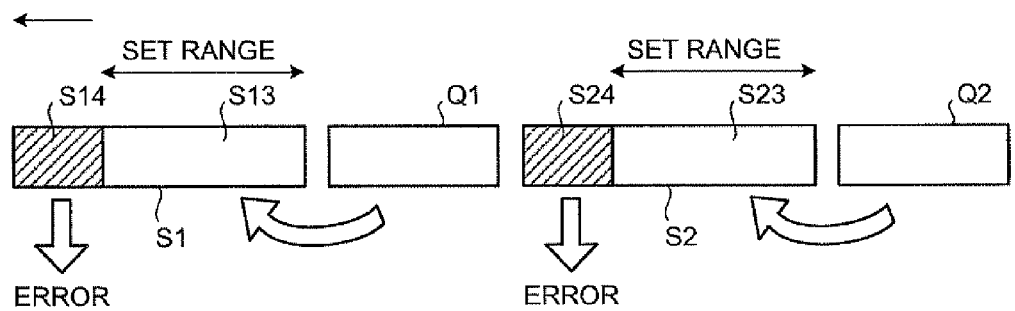
FIG. 17 is a view for illustrating the process operation in the determining unit shown in FIG. 13.
FIG. 18 is a view for illustrating the process operation in the determining unit shown in FIG. 13.

Also, as shown in FIG. 17, in the third embodiment, a predetermined number of samples measured just before the controlled specimen group correspond to the samples within the predetermined set range. As shown in FIG. 17, when the number of samples in the sample group S1 is larger than the predetermined set range, the determining unit 334 reflects the analysis result of the controlled specimen group Q1 to the sample group S13 within the set range measured just before the controlled specimen group Q1 of the sample group S1, and determines all of the analysis results of the sample group S14 out of the set range to be error. Similarly, in the sample group S2 also, the determining unit 334 reflects the analysis result of the controlled specimen group Q2 to the sample group S23 within the set range and determines all of the analysis results of the sample group S24 out of the set range to be error. Specifically, as shown in a table T6 in FIG. 18, when the controlled specimen group Q1 indicates "+" and determined to be normal, the determining unit 334 determines that the analysis results of the sample group S13 within the set range are normal as indicated by an arrow Y33 and determines that all of the analysis results of the specimen group S14 out of the set range are error as indicated by an arrow Y34. Also, when the analysis result of the controlled specimen group Q1 indicates "−" and determined to be abnormal, the determining unit 334 determines that all of the analysis results of the sample group S1 are error as indicated by an arrow Y35.

In this manner, the analyzer 301 automatically generates the analysis information in which each determination result based on the analysis result of the controlled specimen is associated with the analysis results of the specimens, and outputs the same, so that this has the effect similar to that of the first embodiment.

Meanwhile, in the analyzers 1, 201 and 301, the determining units 34, 234 and 334 perform determination for the samples for each item to be analyzed of the controlled specimen. For example, when the controlled specimen group has the controlled specimen indicating the known value for an item to be analyzed "A", and the controlled specimen indicating the known value for an item to be analyzed "B", respectively, the determining units 34, 234 and 334 may reflect the analysis result of the controlled specimen corresponding to the item to be analyzed "A" to the sample group for the item to be analyzed "A", and reflect the analysis result of the controlled specimen corresponding to the item to be analyzed "B" to the sample group for the item to be analyzed "B", respectively. In addition, when the controlled specimen group has a plurality of controlled specimens indicating the known value for the analysis result "A", the determining units 34, 234 and 334 determine that the analysis result of the controlled specimen corresponding to the item to be analyzed "A" is abnormal when determining that there is abnormality in a part of the analysis results of the controlled specimens corresponding to the item to be analyzed "A", and reflects the determination result to the corresponding specimen group. In other words, the determining units 34 and 334 determine that the analysis results of the sample group within the set range are normal when determining that all of the analysis results of the controlled samples corresponding to the item to be analyzed "A" are normal. Also, the determining unit 234 determines that the analysis results of the sample group to be determined are normal when determining that all of the analysis results of the controlled specimens corresponding to the item to be analyzed "A" before and after the sample group to be determined are normal and the number of samples is within the predetermined set range.

In addition, the controlled specimens corresponding to each item to be analyzed are accommodated according to a predetermined accommodation position in a controlled specimen rack in which the controlled specimens are accommodated. In this case, the analyzers 1, 201 and 301 obtain the known analysis results in each controlled specimen by means of the input unit 32, the storage unit 35, and the transmitting/receiving unit 37, and the determining units 34, 234 and 334 determine whether the analysis results of each controlled specimen are normal or not based on the known analysis results in the obtained controlled specimen. Also, the analyzers 1, 201 and 301 may obtain the known analysis results of each controlled specimen by recording the corresponding item to be analyzed and analysis result in the recording medium attached to the controlled specimen rack or the sample vessel 11a in which each controlled specimen is accommodated and reading the information of the recording medium by the sample reader 11c. In this case, it is not required that the controlled specimen corresponding to each item to be analyzed be accommodated according to the predetermined accommodation position.

Each of the determination process contents and the predetermined set range described in the first to third embodiments may be freely selected based on the indication information input from the input unit 32. Also, in the analyzers 1, 201 and 301, when a carrying error in the plate carrier lane 10 and the sample transferring unit 11 occurs in the controlled specimen, the analysis result of the controlled specimen is not treated as determination criteria in the determination process of the analysis result of the samples, and the process is performed following the procedure similar to that in a case in which the analysis result of the controlled specimen is not received at the analyzing unit 33. That is to say, in the output analysis information, the analysis result of the controlled specimen and the determination result based on the analysis result of the controlled specimen are not included, and the user may comprehend the abnormality such as the carrying error by checking such analysis information.

Although the analyzers 1, 201 and 301 according to the first to third embodiments, respectively, have been described by taking the analyzer for performing the immunologic examination such as the antigen-antibody reaction of the test blood using the immunological agglutination behavior as an example, this may be applied to the analyzer for performing the biochemical examination and the blood transfusion examination as long as the analyzer using the controlled specimen.

In addition, the analyzer described in the above-described embodiments may be realized by executing the prepared program by the computer system such as the personal computer and the workstation. Hereinafter, the computer system for executing an analysis program having the function similar to that of the analyzer described in the above-described embodiments is described.

Figure 19:
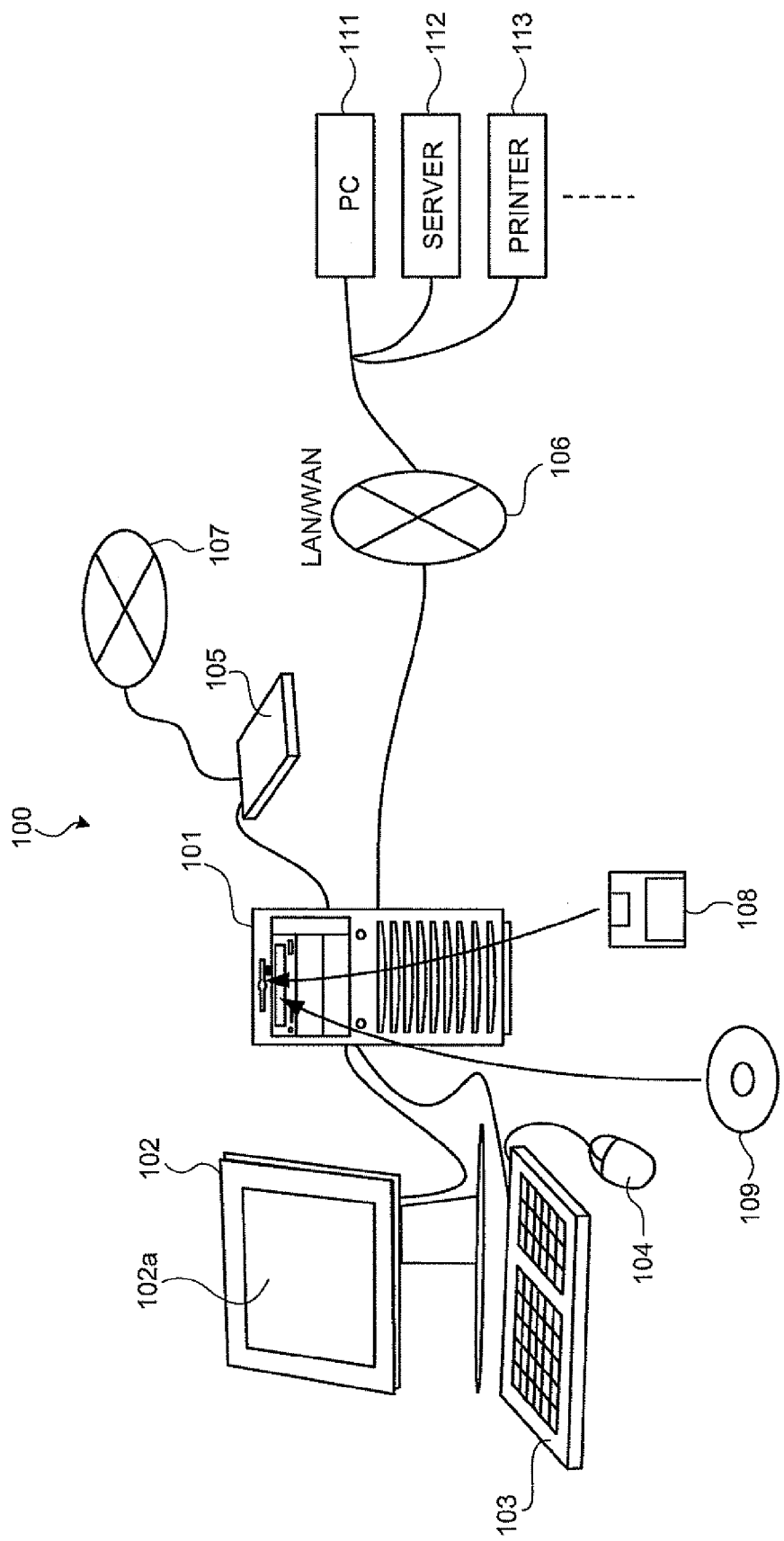
FIG. 19 is a configuration diagram for showing a configuration of a computer system using the embodiment.
Figure 20:
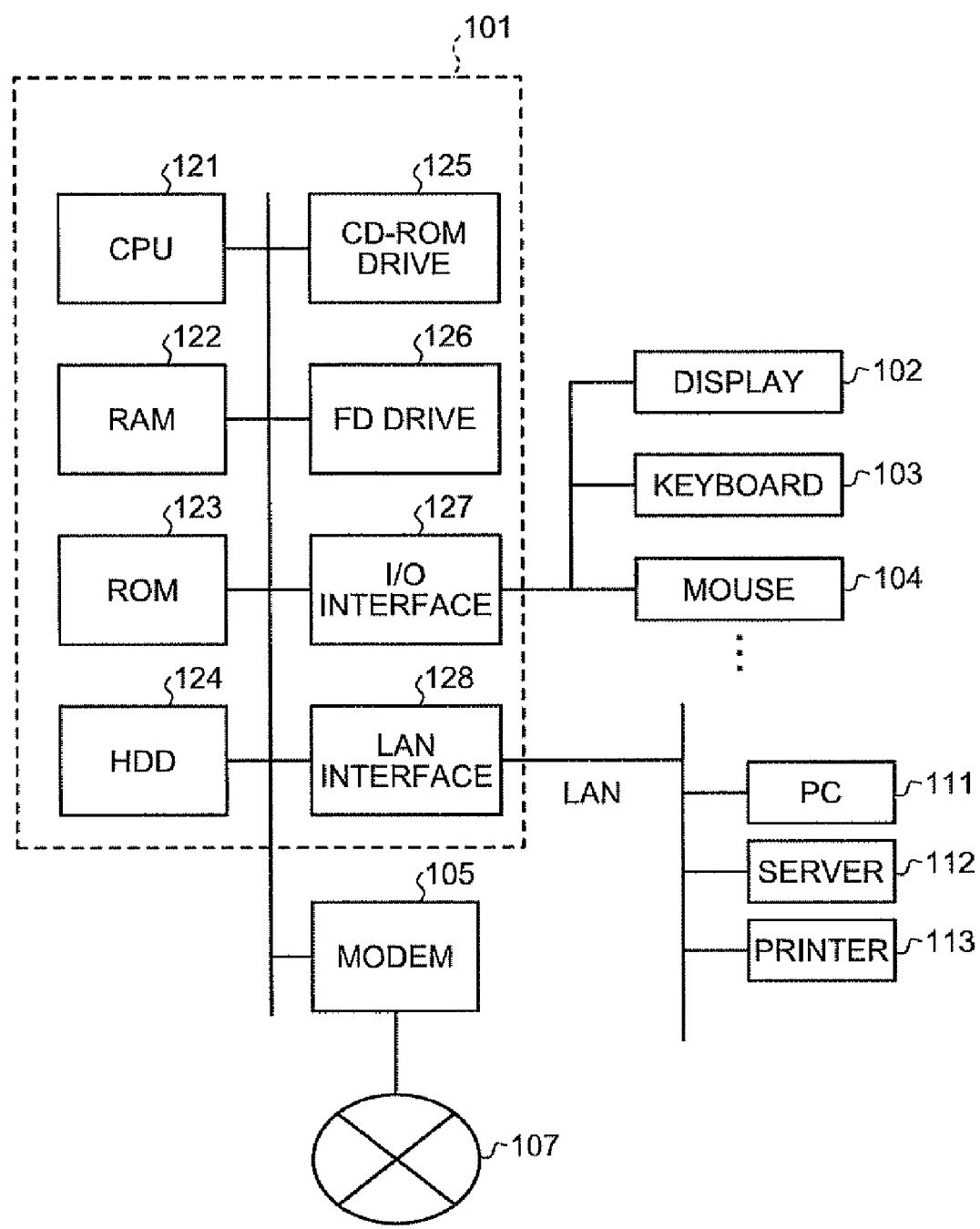
FIG. 20 is a block diagram for showing a configuration of a main body in the computer system shown in FIG. 19.

FIG. 19 is a system configuration diagram for showing a configuration of the computer system using the above-described embodiments, and FIG. 20 is a block diagram for showing a configuration of a main body of the computer system. As shown in FIG. 19, a computer system 100 according to the embodiment is provided with a main body 101, a display 102 for displaying information such as an image on a display screen 102a by an instruction from the main body 101, a keyboard 103 for inputting various pieces of information to the computer system 100, and a mouse 104 for designating an optional position on the display screen 102a of the display 102.

In addition, the main body 101 of the computer system 100 includes a CPU 121, a RAM 122, a ROM 123, a hard disk drive (HDD) 124, a CD-ROM drive 125 that accepts a CD-ROM 109, a FD drive 126 that accepts a flexible disk (FD) 108, an I/O interface 127 that connects the display 102, the keyboard 103, and the mouse 104, and a LAN interface 128 for connecting to a local area network or a wide area network (LAN/WAN) 106.

Further, a modem 105 for connecting to a public line 107 such as an Internet is connected to the computer system 100, and another computer system (PC) 111, a server 112, a printer 113 or the like are connected to the computer system 100 through the LAN interface 128 and the LAN/WAN 106.

Then, the computer system 100 realizes the analyzer by reading the program recorded in a predetermined recording medium and executing the same. Herein, the predetermined recording medium includes any type of recording medium that records the program readable by the computer system 100, such as "portable physical medium" such as the flexible disk (FD) 108, the CD-ROM 109, a MO disk, a DVD disk, a magnetooptical disk, an IC card, "fixed physical medium" such as the hard disk drive (HDD) 124, the RAM 122, the ROM 123, provided inside or outside of the computer system 100, and further "communication medium" that shortly holds the program when transmitting the program such as the public line 107 connected through the modem 105 and the LAN/WAN 106 to which another computer system 111 and the server 112 are connected.

That is to say, the analysis program is computer readably recorded in the recording medium such as the above-described "portable physical medium", "fixed physical medium", and "communication medium", and the computer system 100 realizes the analyzer and the analysis method by reading the analysis program from such recording medium and executing the same. Meanwhile, the analysis program is not limited to be executed by the computer system 100, and the present invention may be similarly applied to the case in which another computer system 111 or the server 112 executes the analysis program, and they work together to execute the analysis program.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An analyzer apparatus comprising:
a determining unit that determines whether an analysis result of a sample corresponding to a controlled specimen having a known value is normal or not based on an analysis result of the controlled specimen;
a generating unit that generates analysis information in which a determination result by the determining unit is associated with each analysis result of samples; and
an output unit that outputs the analysis information generated by the generating unit, wherein
the determining unit determines the analysis result of the sample is normal when the analysis result of the controlled specimen is a known value and the number of samples in a sample group comprising said analyzed sample is within a predetermined range,
the determining unit determines the analysis result of the sample is in error when the analysis result of the controlled specimen is a known value and the number of samples in said sample group is not within said predetermined range, and
the determining unit determines the analysis result of the sample is abnormal when the analysis result of the controlled specimen is not a known value.

2. The analyzer according to claim 1, wherein the determining unit determines that the analysis result of the sample within a predetermined range of the sample corresponding to the controlled specimen is normal when the analysis result of the controlled specimen is the known value, and determines that the analysis result of the sample out of the predetermined range is abnormal.

3. The analyzer according to claim 1, wherein the determining unit determines the analysis result for the sample analyzed after the controlled specimen as the sample corresponding to the controlled specimen.

4. The analyzer according to claim 1, wherein the determining unit determines the analysis result for the sample analyzed before the controlled specimen as the sample corresponding to the controlled specimen.

5. The analyzer according to claim 1, wherein the determining unit determines that the analysis result of the sample is normal when first and second controlled specimens each have the known value and the number of samples analyzed between the first and second controlled specimens is within a predetermined range.

6. The analyzer according to claim 2, wherein the predetermined range is set depending on a content of analysis method for the sample.

7. The analyzer apparatus according to claim 1, further comprising a storage unit that stores the analysis information.

8. An analysis method, performed by an analyzer apparatus, for analyzing a sample and a controlled specimen having a known value, the analysis method comprising:
determining whether an analysis result of the sample corresponding to the controlled specimen is normal or not based on an analysis result of the controlled specimen;
generating analysis information in which a determination result by the determining is associated with each analysis result of samples, the each analysis result being obtained at the determining; and
outputting the generated analysis information, wherein
the analysis result of the sample is determined normal when the analysis result of the controlled specimen is a known value and the number of samples in a sample group comprising said analyzed sample is within a predetermined range,
the analysis result of the sample is determined in error when the analysis result of the controlled specimen is a known value and the number of samples in said sample group is not within said predetermined range, and
the analysis result of the sample is determined abnormal when the analysis result of the controlled specimen is not a known value.

9. A computer program product having a non-transitory computer readable medium including programmed instructions for analyzing a sample and a controlled specimen having a known value, wherein the instructions, when executed by a computer, cause the computer to perform:
determining whether an analysis result of the sample corresponding to the controlled specimen is normal or not based on an analysis result of the controlled specimen;

generating analysis information in which a determination result at the determining is associated with each analysis result of samples, the each analysis result being obtained at the determining; and outputting the analysis information, wherein the analysis result of the sample is determined normal when the analysis result of the controlled specimen is a known value and the number of samples in a sample group comprising said analyzed sample is within a predetermined range, the analysis result of the sample is determined in error when the analysis result of the controlled specimen is a known value and the number of samples in said sample group is not within said predetermined range, and the analysis result of the sample is determined abnormal when the analysis result of the controlled specimen is not a known value.

* * * * *